United States Patent [19]

Yuuchi et al.

[11] Patent Number: 5,109,845

[45] Date of Patent: May 5, 1992

[54] WIRELESS LOW-FREQUENCY MEDICAL TREATMENT DEVICE

[75] Inventors: Takahiro Yuuchi; Yasuyuki Tsuchida; Masakatsu Fujiwara, all of Hyogo, Japan

[73] Assignee: Sanyo Electric Co., Ltd., Osaka, Japan

[21] Appl. No.: 612,732

[22] Filed: Nov. 14, 1990

[30] Foreign Application Priority Data

Nov. 17, 1989 [JP] Japan .................................. 1-299984

[51] Int. Cl.⁵ .............................................. H61N 1/36
[52] U.S. Cl. .................................... 128/421; 128/422; 128/419 R
[58] Field of Search .................. 128/419 R, 421, 422, 128/423 R, 423 W, 424; 600/9, 13–15; 343/702, 742, 788, 867

[56] References Cited

U.S. PATENT DOCUMENTS

| | | | |
|---|---|---|---|
| 4,102,348 | 7/1978 | Hihara et al. | 128/422 |
| 4,372,319 | 2/1983 | Ichinomiya et al. | 128/421 |
| 4,683,389 | 8/1972 | Hollis | 343/788 |
| 4,690,144 | 9/1987 | Rise et al. | 128/419 R |
| 4,699,143 | 10/1987 | Dufresne et al. | 128/419 R |
| 4,873,527 | 10/1989 | Tan | 343/718 |

FOREIGN PATENT DOCUMENTS 2123214  1/1984  United Kingdom .

Primary Examiner—Stephen C. Pellegrino
Assistant Examiner—Steven J. Shumaker
Attorney, Agent, or Firm—Armstrong & Kubovcik

[57] ABSTRACT

A wireless low-frequency medical treatment device having a sending section for sending data for low-frequency medical treatment and a pulse applying section for receiving the above data and applying a low-frequency pulse corresponding to the data on a living body, the device being characterized in that the sending section comprises a plurality of sending coils, whose axes cross each other in a space, and a sending coil driving circuit for supplying the sending coils with resonating currents having different phases, respectively, the currents indicating a signal corresponding to the data; and that the pulse applying section comprises a receiving coil for receiving the signal sent from the sending coils through electromagnetic induction.

3 Claims, 7 Drawing Sheets

WIRELESS LOW-FREQUENCY MEDICAL TREATMENT DEVICE

BACKGROUND OF THE INVENTION (1) Field of the Invention

This invention related to a wireless low-frequency medical treatment device for applying desirable treatment by conveying data for the treatment of a pulse applying section which is pasted on the living body.

(2) Description of the Prior Art

Japanese Patent Publication Laid-Open No. 63-317164 discloses a known low-frequency medical treatment device of this kind, in which data for desirable treatment is conveyed to a pulse applying section pasted on the living body by FM waves.

However, the use of FM waves enlarged the whole device due to the inevitably large size of an antenna for sending and receiving signals. Moreover, the signals cannot be sent in all directions in case of FM waves although it is indispensable because of the pulse applying section is to be pasted at any place on the living body.

SUMMARY OF THE INVENTION

Accordingly, this invention has an object of offering a wireless low-frequency medical treatment device for conveying data for desirable treatment securely from a sending section to a pulse applying section without using an antenna.

This invention has another object of offering a wireless low-frequency medical treatment device for conveying data for desirable treatment securely in whichever direction a pulse applying section may be from a sending section.

The above objects are fulfilled by a wireless low-frequency medical treatment device having a sending section for sending data for low-frequency medical treatment and a pulse applying section for receiving the above data and applying a low-frequency pulse corresponding to the data on a living body, the device being characterized in that the sending section comprises a plurality of sending coils, whose axes cross each other in a space, and a sending coil driving circuit for supplying the sending coils with resonating currents having different phases, respectively, the currents indicating a signal corresponding to the data; and that the pulse applying section comprises a receiving coil for receiving the signal sent from the sending coils through electromagnetic induction.

The sending coil driving circuit may comprise series capacitors, each connected to the sending coil serially for supplying the sending coil with a series resonating current, and a control circuit for alternately turning on and off the series resonating currents in accordance with the data.

The plurality of sending coils may be two sending coils whose axes cross each other with an angle of 90° and the series resonating currents have a 90° phase difference from each other.

The pulse applying section may comprise a pulse generating circuit for generating a low-frequency pulse in accordance with the data received by the receiving coil and a conveying circuit for conveying the pulse to the living body.

According to the above construction, the data is conveyed from the sending section to the pulse applying section through electromagnetic induction. This eliminates the necessity of an antenna but only requires induction coils to be provided in the sending section and the pulse applying section. As a result, a compact device can be obtained.

Also according to the above construction, a plurality of sending coils are arranged in a space with their axes crossing each other and are given data for desirable low-frequency treatment in the form of signals having different phases from one other. Therefore, the sending section expands a magnetic field to all directions. In such a state, the pulse applying section can receive the data from the sending section in whichever direction the pulse applying section may be from the sending section.

DESCRIPTION OF THE DRAWINGS

These and other objects, advantages and features of the invention will become apparent form the following description thereof taken in conjunction with the accompanying drawings which illustrate a specific embodiment of the invention. In the drawings.

DESCRIPTION OF A PREFERRED EMBODIMENT

A construction of an embodiment according to this invention will be described referring to FIGS. 1 through 8. A wireless low-frequency medical treatment device comprises a sending section 100 and a pulse applying section 200. The sending section 100 comprises a key input part 1 and a signal output part 2 (FIG. 3).

Figure 1:
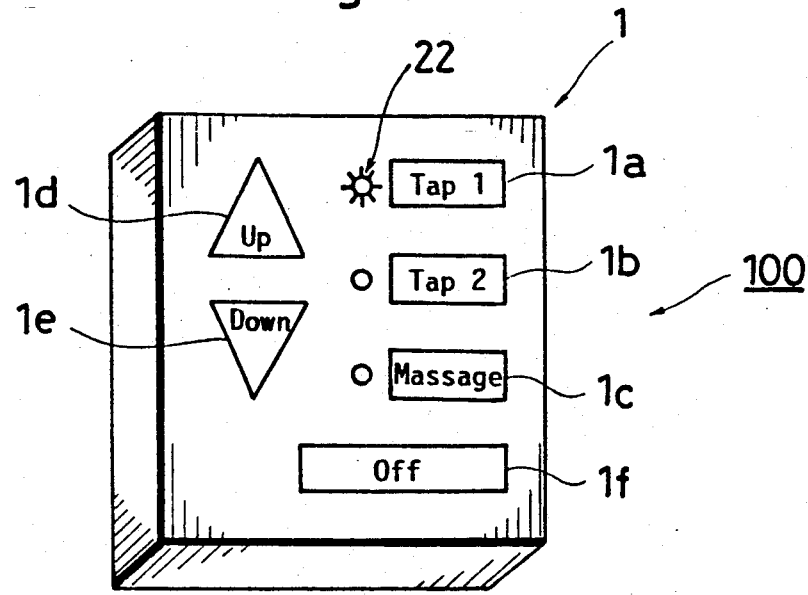
FIG. 1 is an outer view of a sending section of an embodiment according to this invention.

As shown in FIG. 1, the key input part 1 has keys 1a, 1b and 1c respectively for "Tap 1", "Tap 2" and "Massage" modes, keys 1d and 1e respectively for "Up" and "Down", and a key 1f for "Off".

The signal output part 2 comprises a microcomputer 20 as control means for processing data sent from the key input part 1, a converter 21 for converting a signal sent from the microcomputer 20 into a magnetic field, and a display 22 including LEDs for indicating which mode has been selected or the like.

Figure 3:
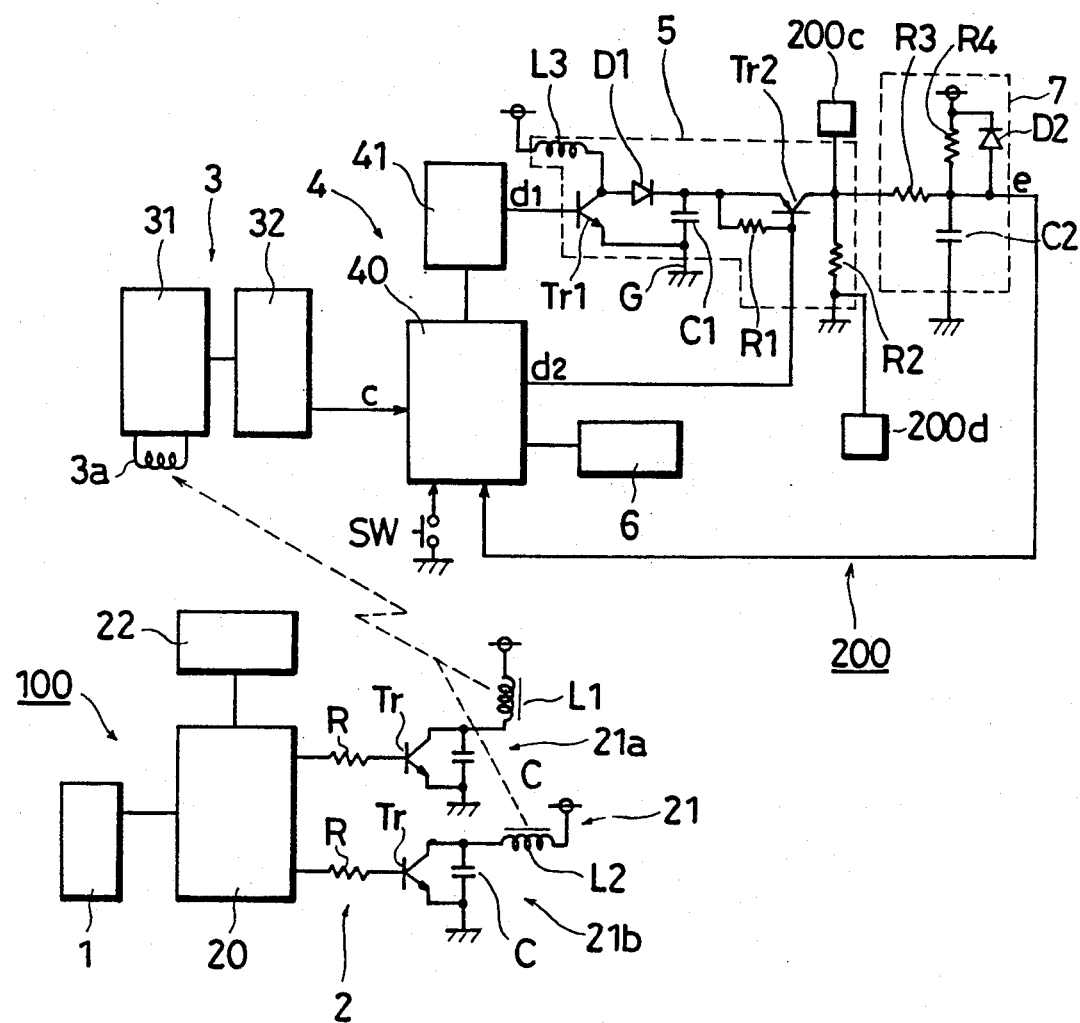
FIG. 3 is a circuit diagram of the embodiment.
Figure 4:
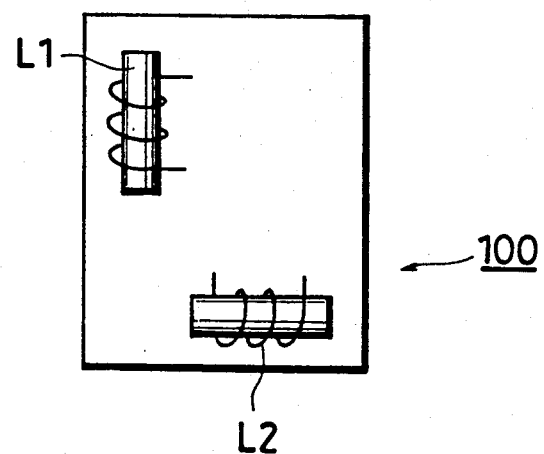
FIG. 4 shows an arrangement of induction coils in the sending section.
Figure 5A:
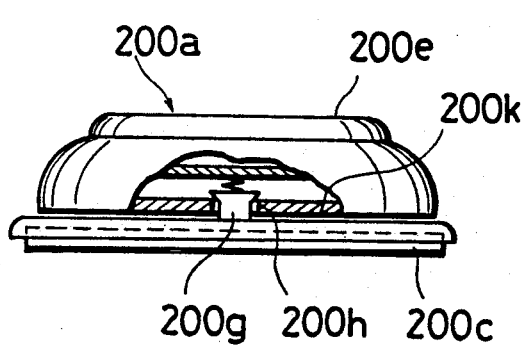
FIG. 5a shows a partial cross section of a pulse applying body.
Figure 5B:
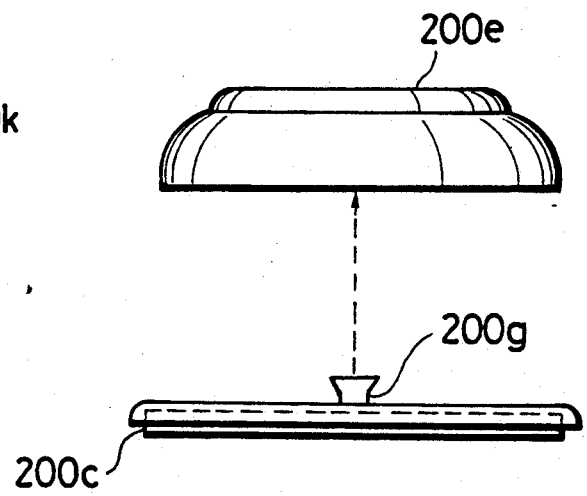
FIG. 5b is a side view of the pulse applying body.

As shown in FIG. 3, the converter 21 is divided into two circuits 21a and 21b, each of which comprises a resistance R, a transistor Tr, a capacitor C and an induction coil L as a sending coil. The resistance R, the transistor Tr and the capacitor C are to function as sending coil driving means. The induction coil of the circuit 21a is referred to as L1 and that of the circuit 21b is referred to as L2. As shown in FIG. 4, the induction coils L1 and L2 are cased in the sending section 100 in the manner that their axes cross each other perpendicularly.

Figure 2A:
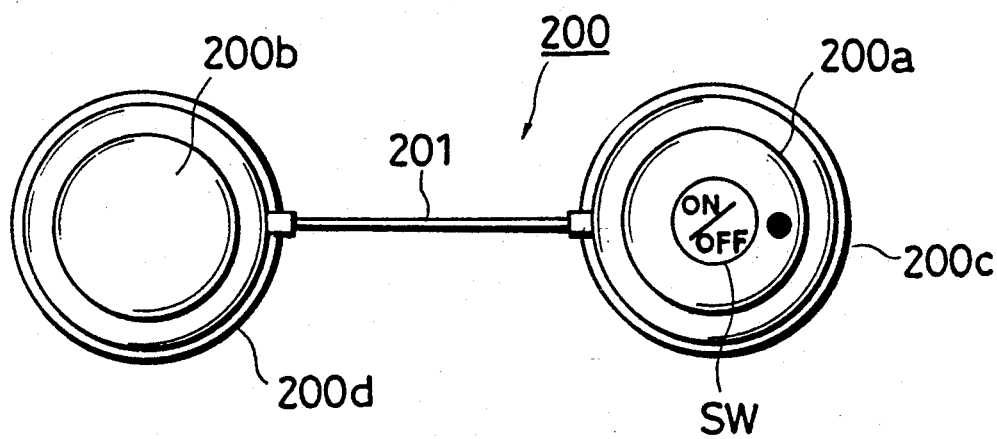
FIG. 2a is a plan view of a pulse applying section of this embodiment.
Figure 2B:
FIG. 2b is a side view thereof.
Figure 6:
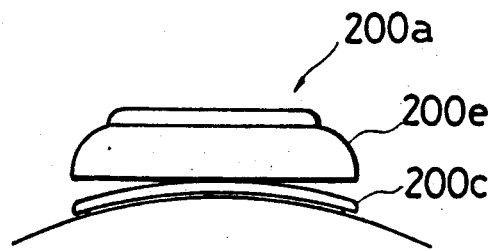
FIG. 6 is a view of a pulse applying body pasted on the human skin.
Figure 7:
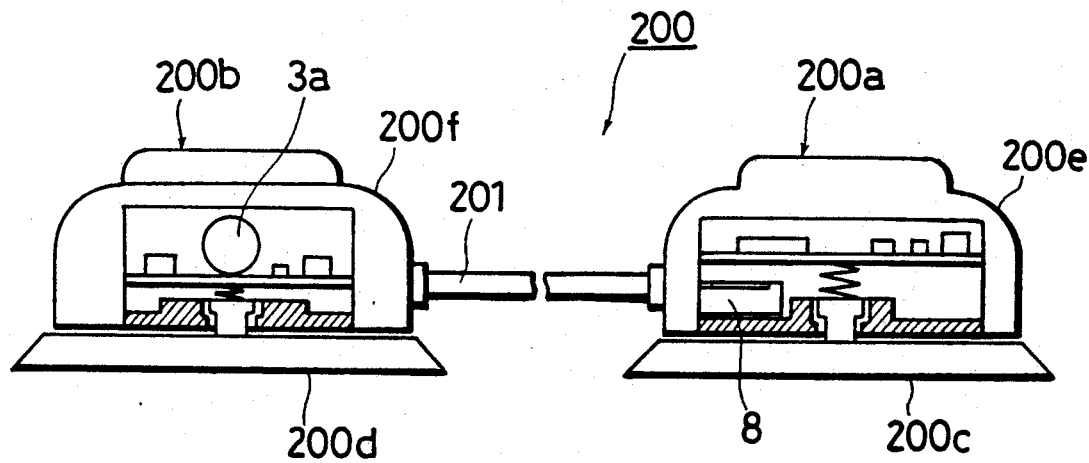
FIG. 7 is a view of circuits inside the pulse applying section.

As shown in FIGS. 2a and 2b, the pulse applying section 200 comprises a pair of pulse applying bodies 200a and 200b and a lead 201 for connecting the bodies. As in FIGS. 5a and 5b, the body 200a can be divided into a pulse applying piece 200c and a cover 200e. The body 200b can also be divided into a pulse applying piece 200d and a cover 200f (FIG. 7). In more detail, the cover 200e has a hole 200h on a bottom surface 200k thereof, into which a projecting portion 200g provided on an upper surface of the piece 200c is engaged. When the piece 200c and the cover 200e are combined, they are electrically connected to each other through the projecting portion 200g. In such construction, when the piece 200c is pasted on the human skin, its lower surface is wholly contacted thereon (FIG. 6). The pulse applying body 200b has the same construction.

In FIG. 3, 3 refers to a relaying circuit, 4 to a signal processor, 5 to a pulse generating circuit, 6 to a beep sounding circuit, and 7 to a skin detector.

The relaying circuit 3 comprises a magnetic/electric converter (will be referred to as the converter) 31 and a low-pass filter 32, the converter 31 being for converting a signal which is sent from the sending section 100 to an induction coil 3a as a receiving coil into an electric signal and the low-pass filter 32 being for taking out data from the electric signal sent from the converter 31.

The signal processor 4 comprises a microcomputer 40 and an oscillator 41. The microcomputer 40 is for sending a signal to the oscillator 41, sending a driving pulse $d_2$ to the pulse generating circuit 5 and controlling the beep sounding circuit 6; and the oscillator 41 is for outputting a driving pulse $d_1$ in accordance with the signal sent from the microcomputer 40.

The pulse generating circuit 5 is for outputting a low-frequency pulse as an electric stimulating pulse in accordance with the driving pulses $d_1$ and $d_2$. The circuit 5 comprises a first transistor Tr1 to be switched by the driving pulse $d_1$, an induction coil L3 connected between a power source and a collector of the first transistor Tr1, a second transistor Tr2 to be switched by the driving pulse $d_2$, a diode D1 connected between the collector of the first transistor Tr1 and an emitter of the second transistor Tr2, a capacitor C1 connected between a cathode of the diode D1 and a ground G, a resistance R1 connected between the emitter and a base of the second transistor Tr2, and a resistance R2 connected between a collector of the second transistor Tr2 and the ground G. Both ends of the resistance R2 are respectively connected to the pieces 200c and 200d.

The skin detector 7 comprises a resistance R3, one end of which is connected to the collector of the second transistor Tr2, a capacitor C2 connected between the other end of the resistor R3 and the ground G, a resistance R4 connected between the above other end of the resistance R3 and a power source, and a diode D2.

The relaying section 3 including the induction coil 3a is integrated in the cover 200f; and the signal processor 4, the pulse generating circuit 5, the beep sounding circuit 6, the skin detector 7, and a cell 8 as the power source are integrated in the cover 200e (FIG. 7). The lead 201 supplies the power from the cell 8 to the relaying circuit 3 as well as supplying a signal from the relaying circuit 3 to the signal processor 4.

Figure 8:
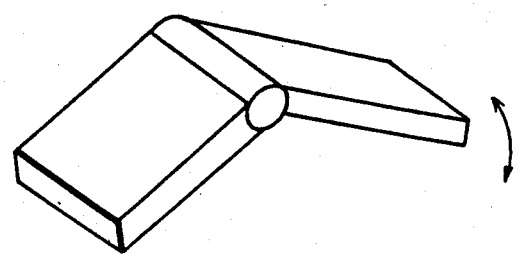
FIG. 8 is a perspective view of another construction of the pulse applying section.

FIG. 8 shows another construction of the pulse applying section, wherein two pulse applying bodies are connected to each other by a hinge.

The wireless low-frequency medical treatment device having the above construction is operated as indicated in FIGS. 9 through 15.

Figure 9:
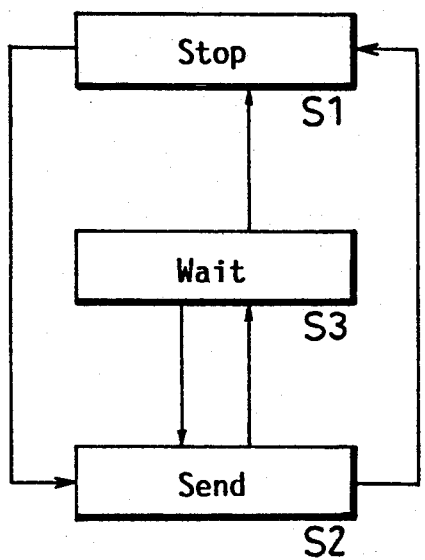
FIG. 9 is a state transition diagram of the sending section.
Figure 10:
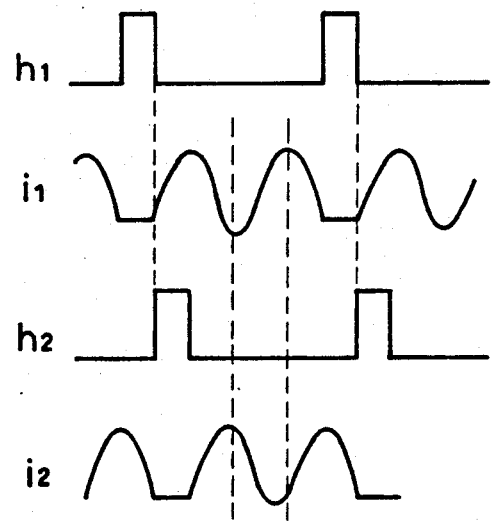
FIG. 10 shows waveforms explaining the operation of converters of the sending section.

FIG. 9 is a state transition diagram of the sending section 100. The microcomputer 20 is stopped in the initial state (S1). When the key 1a, 1b or 1c is pushed, a clock oscillation puts the microcomputer 20 into a sending state (S2), whereby a built-in timer is started. Simultaneously, an LED is lighted up in the display 22 in accordance with the key pushed. If the key 1d or 1e pushed in the initial state, the microcomputer 20 is kept stopped.

When the key 1a for "Tap 1" is pushed, for example, the following operation is executed.

Figure 11:
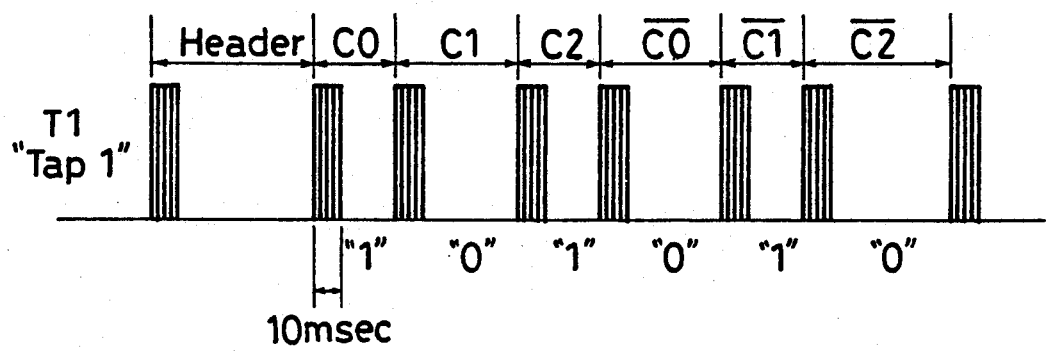
FIG. 11 shows a waveform of a signal sent from the sending section.
Figure 12:
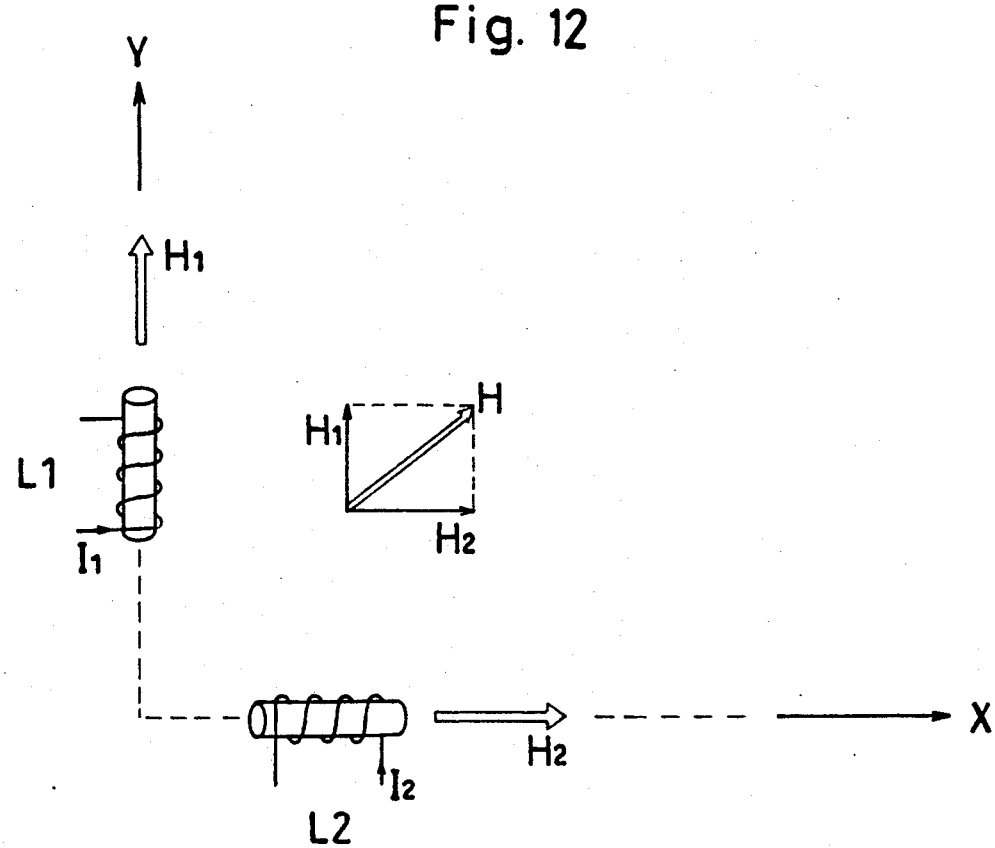
FIG. 12 explains the magnetic field of an induction coil of the sending section.

First, the microcomputer 20 sends corresponding codes $h_1$ and $h_2$ to the converters 21a and 21b, respectively. Since the codes $h_1$ and $h_2$ have different phases (FIG. 10), the inputs of these codes supply the induction coils L1 and L2 and the capacitors C of the converters 21a and 21b with resonating currents $i_1$ and $i_2$, having different phases by 90° ($=\pi/2$(rad)). Then, the induction coils L1 and L2 output a sending signal T1 for "Tap 1" to the converter 31 by a 5 kHz carrier wave. As shown in FIG. 11, the sending signal T1 comprises a header pulse and a pulse code line, wherein [C0 C1 C2 $\overline{C0}$ $\overline{C1}$ $\overline{C2}$] is [101010]. Each pulse is approx. 10 msec wide, and the induction coils L1 and L2 resonate through each pulse. The sending signals T2 through T6 for the other keys have the following pulse code lines.

TABLE 1

|  | C0 | C1 | C2 | $\overline{C0}$ | $\overline{C1}$ | $\overline{C2}$ |
|---|---|---|---|---|---|---|
| Tap 1 (T1) | 1 | 0 | 1 | 0 | 1 | 0 |
| Tap 2 (T2) | 1 | 0 | 0 | 0 | 1 | 1 |
| Massage (T3) | 1 | 1 | 0 | 0 | 0 | 1 |
| Up (T4) | 0 | 1 | 1 | 1 | 0 | 0 |
| Down (T5) | 0 | 0 | 1 | 1 | 1 | 0 |
| OFF (T6) | 0 | 1 | 0 | 1 | 0 | 1 |

Due to the 90° phase difference between the currents $i_1$ and $i_2$, the sending signals from the induction coils L1 and L2 are sent out in all directions uniformly. The reason will be described referring to FIG. 12. Provided a magnetic strength generated by the induction coil L1 is $H_1$ and a magnetic strength generated by the induction coil L2 is $H_2$, $$H_1 = H_{1m}\sin\omega t \quad (1)$$

$$H_2 = H_{2m}\sin\left(\omega t + \frac{\pi}{2}\right) \quad (2)$$
$$= H_{2m}\cos\omega t$$

where $$\omega = 2\pi f$$

f: frequency of the carrier wave
t: time
$H_1$ and $H_2$: in parallel with the axes of L1 and L2

Provided the magnetic strength of the composite magnetic field obtained by $H_1$ and $H_2$ is H, and the vector thereof is $\dot{H}$, $$H = \sqrt{H_1^2 + H_2^2} \quad (3)$$
$$= \sqrt{H_{1m}\sin\omega t + H_{2m}\cos\omega t}$$

$$\dot{H} = H_2 + jH_1 \quad (4)$$
$$= H_{2m}\cos\omega t + jH_{1m}\sin\omega t$$

where $j = \sqrt{-1}$

Provided the angle made by the composite magnetic field and the X axis is $\theta$, (4) is expressed as:

$$\dot{H} = \sqrt{H_1^2 + H_2^2}\, e^{j\theta} \quad (5)$$

where $\theta = \tan^{-1}\frac{H_1}{H_2}$.

With (1), (2) and (3) being substituted into (5), $$\dot{H} = \sqrt{H_{1m}^2\sin^2\omega t + H_{2m}^2\cos^2\omega t}\, e^{j\theta} \quad (6)$$

where $\theta = \tan^{-1}\frac{H_{1m}}{H_{2m}}\tan\omega t$

From the above, the strength and the direction of the composite magnetic field changes periodically with the passage of time. Since the strength of the magnetic field H is, as apparent from (3), continuously a positive number which is not zero even if the value of $\omega$ changes, it is assumed that the composite magnetic field is a rotating ellipse. If $H_1$ and $H_2$ have the same strength, namely, if $H_{1m}=H_{2m}=H_m$, (6) is expressed as:

$$\dot{H} = H_m e^{j\omega t} \quad (7)$$

In other words, the composite magnetic field is a rotating circle. The rotating speed of the composite magnetic field, which corresponds to the frequency f of the carrier wave, is high.

The fact that the composite magnetic field is rotating indicates that its strength at any point on the X-Y plane keeps on changing. Accordingly, the sending section 100 can send data to all directions within 360° by the principle of electromagnetic induction.

When the sending signal is sent out to the converter 31, the microcomputer 20 gets into a waiting state for key input (S3). In this state, any of the keys 1a through 1f can be pushed. Every time the key 1a, 1b or 1c is pushed, the timer of the microcomputer 20 is cleared. When the timer detects a specified period of time has passed, the microcomputer 20 sends a code for "Off" to the converters 21a and 21b and stops operating.

Figure 13:
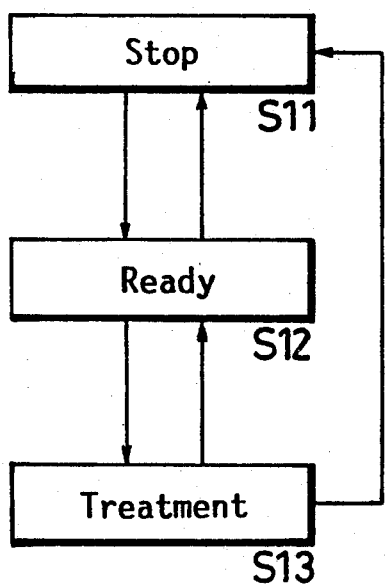
FIG. 13 is a state transition diagram of the pulse applying section.

FIG. 13 is a state transition diagram of the pulse applying section 200. The microcomputer 40 is stopped in the initial state (S11), wherein no command is accepted. When an ON/OFF switch provided on an upper surface of the body 200a is pushed, a built-in clock is oscillated, thereby the microcomputer 40 goes into a ready state (S12), wherein only reception of commands is possible. In the ready state, in other words, a data which is taken out by the low-pass filter 32 from the sending signals sent from the converter 31 is not accepted by the microcomputer 40, but the microcomputer 40 is waiting for an operation command or waiting for a detection signal e outputted by the skin detector 7 to get low. The detection signal e gets low when the pieces 200c and 200d are pasted on the human skin. If the ready state is kept for a specified period (for example, 3 minutes), the microcomputer 40 stops operating in order to prevent the wasted use of the cell 8.

When the key 1a, 1b or 1c is pushed with the detection signal e being low or when the detection signal e gets low with the above key being pushed in the ready state, the microcomputer 40 goes into a treatment state (S13).

Figure 14:
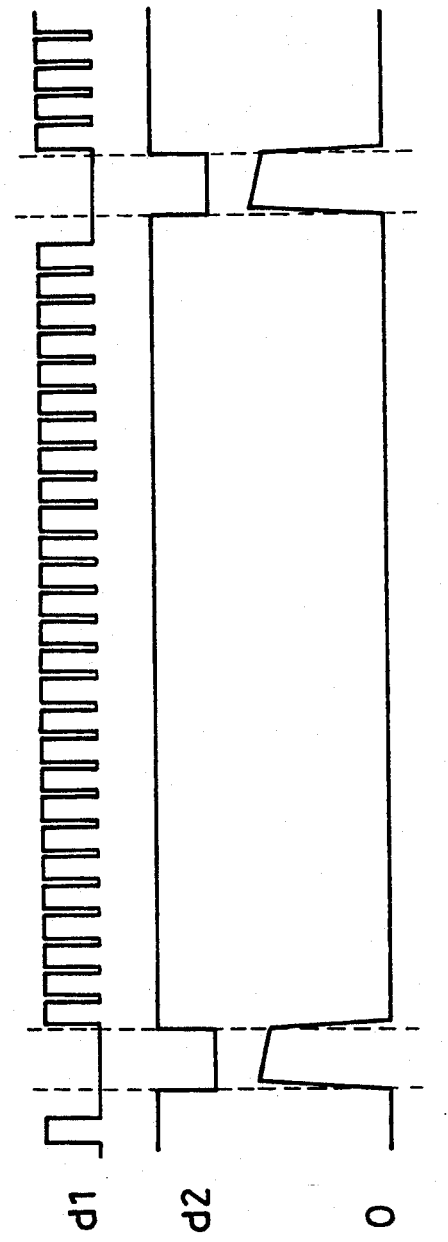
FIG. 14 shows waveforms of driving pulses $d_1$ and $d_2$ and a low-frequency pulse when the number of the driving pulse $d_1$ is large.

In the treatment state, the oscillator 41 is operated in accordance with a data sent from the low-pass filter 32, and a driving pulse $d_2$ is sent to the pulse generating circuit 5. Simultaneously, the microcomputer 40 sends a signal to the beep sounding circuit 6, thereby to emit one (for example) beep. The oscillator 41 sends a driving pulse $d_1$ to the first transistor Tr1 of the pulse generating circuit 5 in accordance with a signal from the microcomputer 40 (FIG. 14). The first transistor Tr1 is turned on or off by the driving pulse $d_1$, thereby to allow an exciting current to be sent from the power source to the induction coil L3 intermittently. Voltages enhanced by the exciting current are accumulated in the capacitor C1 through the diode D1. When the driving pulse $d_2$ gets low, the second transistor Tr2 is turned on. Accordingly, the voltages accumulated in the capacitor C1 are applied on the human skin as low-frequency stimulating pulses O, the human skin being between the pieces 200c and 200d.

Figure 15:
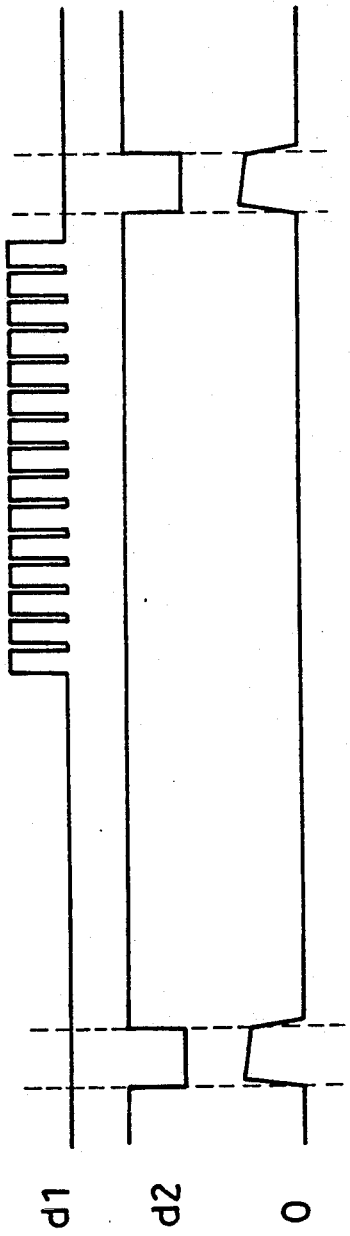
FIG. 15 shows waveforms of driving pulses $d_1$ and $d_2$ and a low-frequency pulse when the number of the driving pulse $d_1$ is small.

The driving pulse $d_1$ is outputted to the first transistor Tr1 when the driving pulse $d_2$ is not outputted. As the number of the driving pulse $d_1$ is reduced, the voltages accumulated in the capacitor C1 are reduced, thereby the stimulating pulses O applied on the human skin are weakened as shown in FIG. 15.

The strength of the stimulating pulses O is determined by the operation of the key 1d or 1e. In more detail, if the key 1d is pushed, for example, the microcomputer 40 commands the oscillator 41 to strengthen the driving pulse $d_1$ and also commands the beep sounding circuit 6 to emit beeps in a way predetermined for "Up"

If the piece 200c or 200d is peeled off from the human skin during treatment, the detection signal e from the skin detector 7 gets high, thereby the microcomputer 40 stops operating and goes into the ready state. If a stop is commanded during the treatment, the microcomputer 40 also goes into the ready state. If the ready state is kept for a specified period of time (for example, 3 minutes), the microcomputer 40 stops operating. If the ON/OFF switch is pushed during treatment, the microcomputer 40 stops operating and the output of the driving pulse $d_2$ is stopped. When none of the above occurs, the microcomputer 40 carries out the treatment for a specified period of time (for example, 15 minutes) after receiving the data for "Tap 1", "Tap 2" or "Massage" and then goes into the ready state.

Although the relay circuit has one induction coil for receiving sending signals from the sending section in this embodiment, two induction coils may be provided.

Although the magnetic fields of the induction coils $L_1$ and $L_2$ have the phase difference of $\pi/2$(rad) in the above embodiment, other angles are usable. However, if these two magnetic fields have no phase difference or if the difference is $\pi$(rad), the composite magnetic field is not rotating but exists only on a straight line passing through the origin. Therefore, if the pulse applying section is off the straight line, the sending signal cannot be sent to the pulse applying section both theoretically and practically. Accordingly, the phase difference should be set other than zero and $\pi$(rad).

The induction coils $L_1$ and $L_2$ cross each other perpendicularly in the above embodiment. However, other arrangements are possible as long as their axes cross each other at an arbitrary angle since such an arrangement can rotate the magnetic field. It is desirable that $L_1$ and $L_2$ cross perpendicularly and are driven with the phase difference of $\pi/2$(rad) in order to send the data signal to all the directions on the X-Y plane at a uniform strength.

Instead of two induction coils as in the above embodiment, three of them can also be used in the sending section. If three induction coils are arranged so that their axes cross perpendicularly one another, the signal can further be sent in the Z direction. Usually, two is enough because the composite magnetic field generally include some Z components.

Although the present invention has been fully described by way of an embodiment with references to the accompanying drawings, it is to be noted that various changes and modifications will be apparent to those skilled in the art. Therefore, unless otherwise such changes and modifications depart from the scope of the present invention, they should be construed as being included therein.

What is claimed is:

1. A wireless low-frequency medical treatment device having a sending section for sending data for low-frequency medical treatment and a pulse applying section for receiving the above data and applying a low-frequency pulse corresponding to the data on a living body, the device comprising:

a sending section comprising a plurality of sending coils, whose axes cross each other in a space, and sending coil driving means for supplying the sending coils with resonating currents having different phases, respectively, the currents indicating a signal corresponding to the data; and a pulse applying section comprising a receiving coil for receiving the signal sent from the sending coils through electromagnetic induction, means for providing the signal to a microcomputer to control low frequency medical treatment applied to a living body by said pulse applying section, and pulse applying bodies for applying the medical treatment.

2. A device of claim 1, wherein the sending coil driving means comprises series capacitors, each connected to a sending coil serially for supplying the sending coils with a series resonating current, and control means for alternately turning on and off the series resonating currents in respective sending coils in accordance with the data.

3. A device of claim 2, wherein the plurality of sending coils are two sending coils whose axes cross each other with an angle of 90° and the series resonating currents have a 90° phase difference from each other.

* * * * *